United States Patent
de Groot et al.

(10) Patent No.: US 9,603,354 B2
(45) Date of Patent: *Mar. 28, 2017

(54) PROTECTIVE SOLUTIONS FOR ORGANS

(75) Inventors: Herbert de Groot, Duesseldorf (DE); Ursula Rauen, Essen (DE); Gernot Koehler, Alsbach-Haehnlein (DE); Wilfried Bruns, Biblis (DE)

(73) Assignee: DR. FRANZ KOEHLER CHEMIE GMBH, Alsbach-Haehnlein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/152,056

(22) Filed: Jun. 2, 2011

(65) Prior Publication Data

US 2011/0300237 A1 Dec. 8, 2011

Related U.S. Application Data

(63) Continuation of application No. 10/438,977, filed on May 16, 2003, now Pat. No. 7,977,383.

(30) Foreign Application Priority Data

May 17, 2002 (DE) .................................. 102 22 561

(51) Int. Cl.
*A01N 1/00* (2006.01)
*A01N 1/02* (2006.01)

(52) U.S. Cl.
CPC ............. *A01N 1/02* (2013.01); *A01N 1/0205* (2013.01); *A01N 1/0226* (2013.01)

(58) Field of Classification Search
None
See application file for complete search history.

(56) References Cited

U.S. PATENT DOCUMENTS

| | | | |
|---|---|---|---|
| 4,415,556 A | 11/1983 | Bretschneider | |
| 4,419,365 A | 12/1983 | McLachlan | |
| 4,562,006 A | 12/1985 | Connor et al. | |
| 4,604,407 A * | 8/1986 | Haslanger et al. | 514/575 |
| 5,290,766 A * | 3/1994 | Choong | A61K 33/14 |
| | | | 128/897 |
| 5,405,742 A * | 4/1995 | Taylor | 435/1.2 |
| 5,498,427 A * | 3/1996 | Menasche | 424/678 |
| 5,506,266 A * | 4/1996 | Davies et al. | 514/575 |
| 6,080,730 A * | 6/2000 | Lemasters et al. | 514/46 |
| 7,977,383 B2 | 7/2011 | de Groot et al. | |

FOREIGN PATENT DOCUMENTS

| | | |
|---|---|---|
| EP | 0 012 272 A1 | 11/1979 |
| EP | 0 054 635 A1 | 10/1981 |
| EP | 0326987 | 8/1989 |
| EP | 161939 B1 | 7/1993 |
| JP | 58121213 | 7/1983 |
| JP | 1265022 | 10/1989 |
| JP | 03294201 | 12/1991 |
| JP | 04128201 | 4/1992 |
| JP | 11514326 | 12/1999 |
| WO | WO 88/09168 | 12/1988 |
| WO | WO 91/15215 | 10/1991 |
| WO | WO 92/04023 A1 * | 3/1992 |
| WO | WO 92/08453 | 5/1992 |
| WO | WO 92/08453 A1 | 5/1992 |
| WO | WO 99/36055 A1 | 7/1999 |
| WO | WO 00/64254 A1 * | 11/2000 |

OTHER PUBLICATIONS

O'Dowd et al. "Analysis of Novel Imidazoles from Isolated Perfused Rabbit Heart by Two High-Performance Liquid Chromatographic Methods". Journal of Chromatography, 577 (1992):347-353.*
Tominaga et al. "Protective Effects of Glutamate and Aspartate on the Ischemic and Reperfused Myocardium of Hearts from Starved Rats." Japanese Journal of Surgery, 15(5); 1985:387-394.*
Loganathan et al. "Effects of Custodiol-N, a Novel Organ Preservation Solution, on Ischemia/Reperfusion Injury". Journal of Thoracic and Cardiovascular Surgery. Apr. 2010; 139:1048-1056.*
't Hart et al. "New Solutions in Organ Preservation". Transplantation Reviews. Jul. 2002, 16(3):131-141.*
Prabhakar et al. "Reactions Between Hydroxylamines and Aroyl Cyanides". Tetrahedron Letters. 1982; 23(13):1391-1394. [Abstract Only].*
Organic Synthesis Collective, vol. V, pp. 623-626.
Houben-Weyl, Methods for Organic Chemistry, pp. 686-688.
A. Kleemann, J. Engel, Pharmaceutical Active Agents, 2nd Ed., 1982, pp. 206-207.
MacFarlane et al., "Synergism of Histidyl Dipeptides as Antioxidants," J. Mol. Cell Cardiol., 1991, 23:1205-1207.

* cited by examiner

*Primary Examiner* — Leslie A. Royds Draper
(74) *Attorney, Agent, or Firm* — Fish & Richardson P.C.

(57) ABSTRACT

Described is a protective solution for avoiding ischemic, storage or ischemia/reperfusion to organs, or to isolated cell systems, or to tissue components after perfusion, surgery, transplantation, or cryopreservation and subsequent reperfusion, which contains alkali ions, and if need be also alkaline earth ions as the electrolyte, a buffer e.g. on a histidine derivation basis, as well as a polyol and/or a saccharide, has an osmolarity of about 290 mosm/l to about 350 mosm/l, as well as a pH value of about 6.8 to about 7.4, and to which hydroxamic acid, and/or one or more hydroxamic acid derivatives are added.

5 Claims, 6 Drawing Sheets

PROTECTIVE SOLUTIONS FOR ORGANS

This application is a continuing application of U.S. application Ser. No. 10/438,977, filed May 16, 2003, now U.S. Pat. No. 7,977,383 and further claims priority from German Application DE 102 22 561.3, filed May 17, 2002, the disclosures of which are hereby incorporated by reference.

The invention at hand relates to an improved composition of solutions for organ protection, preferably the protection of heart, lungs, kidneys, liver, pancreas, and vascular systems in order to be able to perform operations of longer durations on ischemic organs not supplied by blood, as the case may be, for the preservation of the said organs for transplantation with reduced tissue damage as opposed to other preservation methods during the transport, or storage time, respectively, or for the reperfusion of ischemic organs. The invention at hand provides suitable solutions, as well as methods for the production in accordance with the requirements of GMP guidelines.

With the introduction of the hyperkalaemic cardiac arrest by Melrose in the year 1955, heart surgeons were able to perform complex procedures on the ischemic, non-beating heart. Although surgery could last only 40 minutes with the cardioplegic solutions back then, initial surgical reconstructions in the case of congenital heart abnormalities and the use of heart valve prostheses were possible. Banard set a milestone in heart surgery in 1967 with the first heart transplant performed.

The goal of further research was to prolong the current limited operation time with suitable solutions and respective application methods. In the sixties already, the work group of Bretschneider was able to substantially prolong the ischemia times using new concepts for the improvement of myocardium protection. For the first time, a cardiac arrest was induced by means of the withdrawal of sodium, and the cell membrane was protected with compounds, such as procain, acetylcholin, and Novocain in order to counteract the development of an intracellular edema.

A preservation solution for heart, kidneys, and other organs is described in the European Patent Application 12272, which is characterized by a buffer system on the basis of histidine+histidine-HCl, and which also contains sodium, potassium, and magnesium ions, as well as a polyol, or a saccharide. The tolerable ischaemia time is achieved by the factor 8 as opposed to the times of untreated hearts with this protective solution.

A further improvement of this solution is described in the European Patent Application 54635, according to which the ATP loss of the aerobic metabolism is reduced during the approximately 8 to 10 minute long perfusion of the organ with the protective solution by means of favorably influencing the citrate cycle by adding alpha-ketoglutarate. In the years following, clinicians and physiologists directed their attention to the time phase of the ischaemia completion, which ends with the warming of the hypothermic and hypoxic organ, and the reperfusion with blood, and in which the organs regain their full functions. Studies have shown that especially during the so-called reperfusion phase, different pathophysiological processes occur, which are summarized by the term reperfusion damage (I-R damage). In particular, endothelial cell damage occurs, which is interpreted partially as the cause, partially as the result of inflammatory processes, and in the pathogenesis of which reactive oxygen species seem to be of significant importance. Additionally, during recent years, the hypothermia used for the protection of the organs was found to be a trigger of cell injury none of the currently used preservation solutions is able to provide protection from.

The purpose of the invention at hand is to avoid, or reduce the following pathophysiological procedures during ischaemia and reperfusion:

Ischemic damage
Hypothermic injury (cold-induced apoptosis)
Reperfusion damage
Inflammatory processes.

For this purpose, an organ-protective solution is a protective solution for avoiding ischemic storage or ischemia/reperfusion injury to organs, or to isolated cell systems, or to tissue components after perfusion, surgery, transplantation, or cryopreservation and subsequent reperfusion, which contains alkali ions, and if need be also alkaline earth ions as the electrolyte, a buffer, as well as a polyol, and/or a saccharide, has an osmolarity of about 290 mosm/l to about 350 mosm/l, as well as a pH value of about 6.8 to about 7.4, and to which hydroxamic acid, and/or one or more hydroxamic acid derivatives are added, or alternatively, is a protective solution for avoiding ischemic storage or ischemia/reperfusion injury to organs, or to isolated cell systems, or to tissue components after perfusion, surgery, transplantation, or cryopreservation and subsequent reperfusion, which contains alkali ions, and if need be also alkaline earth ions as the electrolyte, a buffer on the basis of one or more histidine derivatives, as well as a polyol, and/or a saccharide, and which has an osmolarity of about 290 mosm/l to about 350 mosm/l, as well as a pH value of about 6.8 to about 7.4, which serves to fulfill the said task. The illustrated mechanisms of the cell and tissue damage in cardioplegia and organ preservation result in a series of requirements for the compound of an organ protection solution. In realizing these requirements, we have found substances that allow the conception of a new, effective organ protection solution according to the above. The compound of the solution is chosen so that it provides an effective protection especially for the aforementioned damage components. The preservation damage can be significantly reduced by means of the mechanism-oriented and non-toxic components. The toxicity of the currently used preservation solutions known to occur with the rewarming of the organ (accidental, or occurring during the anastomosis time) is avoided. In this way, functionality and viability of the respective organ tissue are improved, and the ischaemia and cold storage tolerance is increased; thus enabling longer organ preservation times. This can also contribute to logistics in order to improve the availability of organs for transplants.

Figure 1:
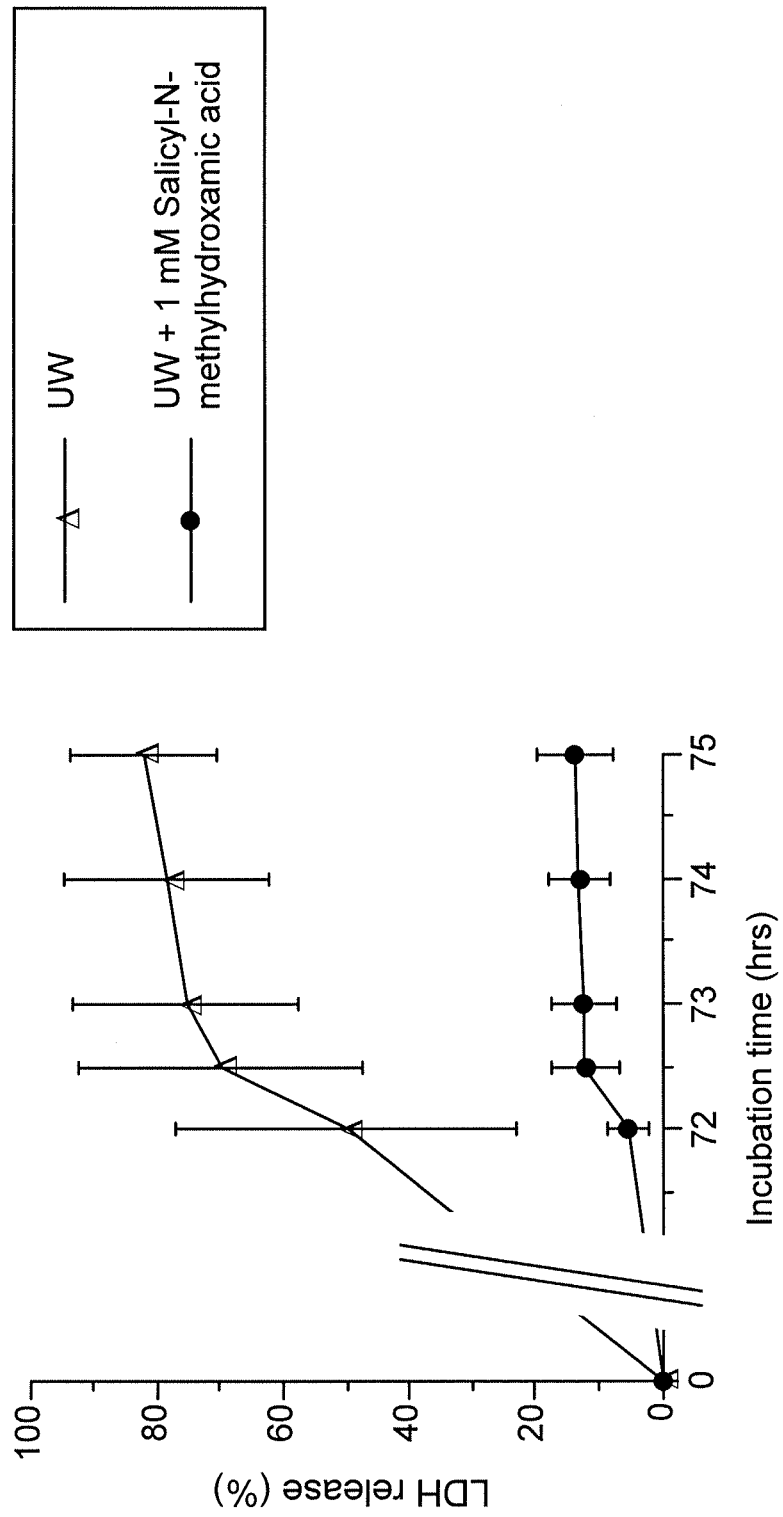
FIG. 1 is a graph showing the inhibition of hypothermic injury of liver endothelial cells by means of salicyl-N-methylhydroxamic acid.

It is recommended that a hydroxamic acid derivative is used, wherein the hydrogen atom at the hydroxamic acid nitrogen is substituted by alkyl, aryl or alkylaryl-groups with $C_1$ to $C_{20}$.

Preferably in the hydroxamic acid derivative, the hydrogen atom at the hydroxamic acid carbon is substituted by alkyl, aryl or alkylaryl-groups with $C_1$ to $C_{20}$, the substituent optionally also containing heteroatoms and/or hydroxy-, amino-, methoxy-groups.

Moreover, the substituents in the hydroxamic acid nitrogen may be closed to a ring together with the substituents in the hydroxamic carbon.

Good results are obtained when using a solution which contains one or more of the compounds and/or their salts from the group
  acethydroxamic acid,
  acet-N-methylhydroxamic acid,
  N-benzylacethydroxamic acid,
  hexanehydroxamic acid
  hexane-N-methylhydroxamic acid,
  benzohydroxamic acid,
  N-methylbenzohydroxamic acid,
  salicylhydroxamic acid,
  salicyl-N-methylhydroxamic acid,
  salicyl-N-benzylhydroxamic acid,
  2-phenylacethydroxamic acid,
  2-phenylacet-N-methylhydroxamic acid,
  3,4-dimethoxybenzohydroxamic acid
  3,4-dimethoxy-N-methyl-benzohydroxamic acid
  2,3-dihydroxybenzohydroxamic acid
  2,4-dihydroxybenzohydroxamic acid
  3,5-dimethoxy-N-methyl-benzohydroxamic acid
  2,4-dihydroxybenzohydroxamic acid
  2,3-dihydroxybenzohydroxamic acid
  3,4-dihydroxybenzohydroxamic acid
  3,4,5-trimethoxy-benzohydroxamic acid
  3,4,5-trimethoxy-N-methyl-benzohydroxamic acid
  4-hydroxy-3-methoxy-benzohydroxamic acid
  2-hydroxy-3-methoxy-benzohydroxamic acid
  2-hydroxy-5-methoxy-benzohydroxamic acid
  2-hydroxy-3-methyl-isocarbostyril
  4-chloro-N-methyl-benzohydroxamic acid
  6-cyclohexyl-1-hydroxy-4-methyl-2(1H)-pyridone.

In a preferred embodiment of the invention to the solution deferoxamin is added.

It is further recommended to add a derivative of 6-hydroxy-2,5,7,8-tetramethylchromane-2-carboxylic acid, preferably of the respective methylester to the solution.

The invention provides also for a protective solution for avoiding ischemic storage or ischemia/reperfusion injury to organs, or to isolated cell systems, or to tissue components after perfusion, surgery, transplantation, or cryopreservation and subsequent reperfusion, which contains alkali ions, and if need be also alkaline earth ions as the electrolyte, a buffer on the basis of one or more histidine derivatives, as well as a polyol, and/or a saccharide, and which has an osmolarity of about 290 mosm/l to about 350 mosm/l, as well as a pH value of about 6.8 to about 7.4.

Preferably the solution contains a buffer on the basis of N-acetylhistidine.

In a further embodiment of the invention, a buffer on the basis of N-acetylhistidine is selected, if need be in combination with a suitable organic base, such as N-glycylhistidine/N-glycylhistidine-hydrochloride, or N-acetylhistidinelysine, and/or -arginine and/or -choline.

It is preferred to select a cation content of lysine, and/or lysine derivative, preferably dipeptides containing lysine and/or an anion content of aspartate.

Hydroxamic acid, and/or its derivatives may be contained in the solution at a concentration of up to about 10 mmol/l.

Moreover, deferoxamine may be contained in the solution at a concentration of up to about 10 mmol/l.

The trolox or trolox derivative may be contained in the solution at a concentration of up to about 10 mmol/l.

It is also preferred that the N-acetylhistidine or the N-glycylhistidine- is contained at a concentration of about 20 mmol/l to about 265 mmol/l.

Also sodium may be purposefully contained in the solution as electrolyte at a concentration of about 10 mmol/l to about 120 mmol/l.

Moreover, potassium may be purposefully contained as the electrolyte at a concentration of about 5 mmol/l to about 25 mmol/l.

Furthermore magnesium may be purposefully contained in the solution at a concentration of about 3 mmol/l to about 27 mmol/l.

Preferably calcium may be purposefully contained in the solution at a free concentration of about 0.0001 mmol/l to about 1.5 mmol/l.

Lysine, and/or its derivatives, preferably a dipeptide containing lysine may be purposefully contained in the solution as the cation at a concentration of up to about 140 mmol/l.

Preferably, aspartate may be contained at a concentration of up to about 140 mmol/l.

The solution may also contain chloride and it is preferred that aspartate is contained at a ratio in excess of chloride.

Moreover, alpha-ketoglutarate may purposefully be contained in the solution at a concentration of about 1 mmol/l to about 9 mmol/l.

Advantageously an osmolyte may purposefully be contained at a concentration of up to about 140 mmol/l.

The invention provides also for a method for the production of an above described solution, wherein the electrolytes are stirred until they are dissolved in an excess of water, purposefully in about 90% of the required amount of water, the buffer, and subsequently the hydroxamic acid, and/or their derivatives are added, the pH value is then adjusted, the osmolyte(s) is/are added, and the solution is then adjusted with water to the desired volume.

In an embodiment of the method, short chain alcohols, and/or DMF, and/or THF are used as solvents for the production of hydroxamic acid, and/or its derivatives, and it is recommended that the reaction is performed base-catalyzed with a carboxylic acid ester.

The hydroxamic acid derivates in the above solutions may be used for the protection against ischemic or reperfusion injuries, e.g. following infarcts or other inflammatory reactions.

The above identified solutions are for use against reperfusion injuries following heart diseases, heart attack, apoplexy, accident surgery or extremity reperfusion, and/or for use in therapy of diseases caused by hyperferrency (e.g. Alzheimer) and/or for use in therapy of cell damages by radicals, oxygen radicals or $H_2O_2$.

Iron-chelating agents may serve for the inhibition of the iron-dependent hypothermic injury, or of the cold-induced apoptosis. Not every complexing agent is suitable as the compound in order to avoid this type of cell damage. For instance, EDTA, as well as the histidine contained in Custodiol is ineffective in this case, although these ligands also form strong iron complexes. Rather, iron must be bound by the ligand in a special way, and the ligand must reach the intracellular compartments quickly, and at a sufficient concentration.

It was shown that the structural element of the hydroxamic acid I or II, which is contained three times in deferoxamin, is of special importance as a suitable structural element, or ligand for iron,

whereby $R^1=C_1-C_{20}$ alkyl, aryl, alkyl-aryl means straight chained or branched, also heteroatoms, and/or additional substituents, such as —OH, —NH$_2$, etc. can be contained, $R^2$=H, or is otherwise like $R^1$, and whereby $R^1$ and $R^2$ can be closed to a ring, and/or can contain additional substituents; such as 2-hydroxypyridine-N-oxide and its derivatives, which merely represent another tautomeric structure of the case, whereby $R^1$ and $R^2$ are closed to a ring with conjugated double bonds. With the substances that are small and lipophilic as opposed to deferoxamin, the strategy of a rapid intracellular availability of a strong iron-chelating agent is verified.

Simple hydroxamic acids also show a positive effect; but a certain hydrophilicity/lipophilicity ratio is required for a good effect. In addition to that it was shown that compounds that are alkyl-substituted at the hydroxamic acid nitrogen ($R^2$=alkyl) are generally more effective as opposed to non-substituted compounds ($R^2$=H). If $R^1$ is a strongly electron-pulling group, such as CO—$R^3$ ($R^3$ has the same meaning as $R^1$), this leads to ineffectiveness, even though these compounds also easily form iron complexes, such as:

N-hydroxysuccinimide
3,4-dihydro-3-hydroxy-4oxo-1,2,3-benzotriazine.

Figure 2:
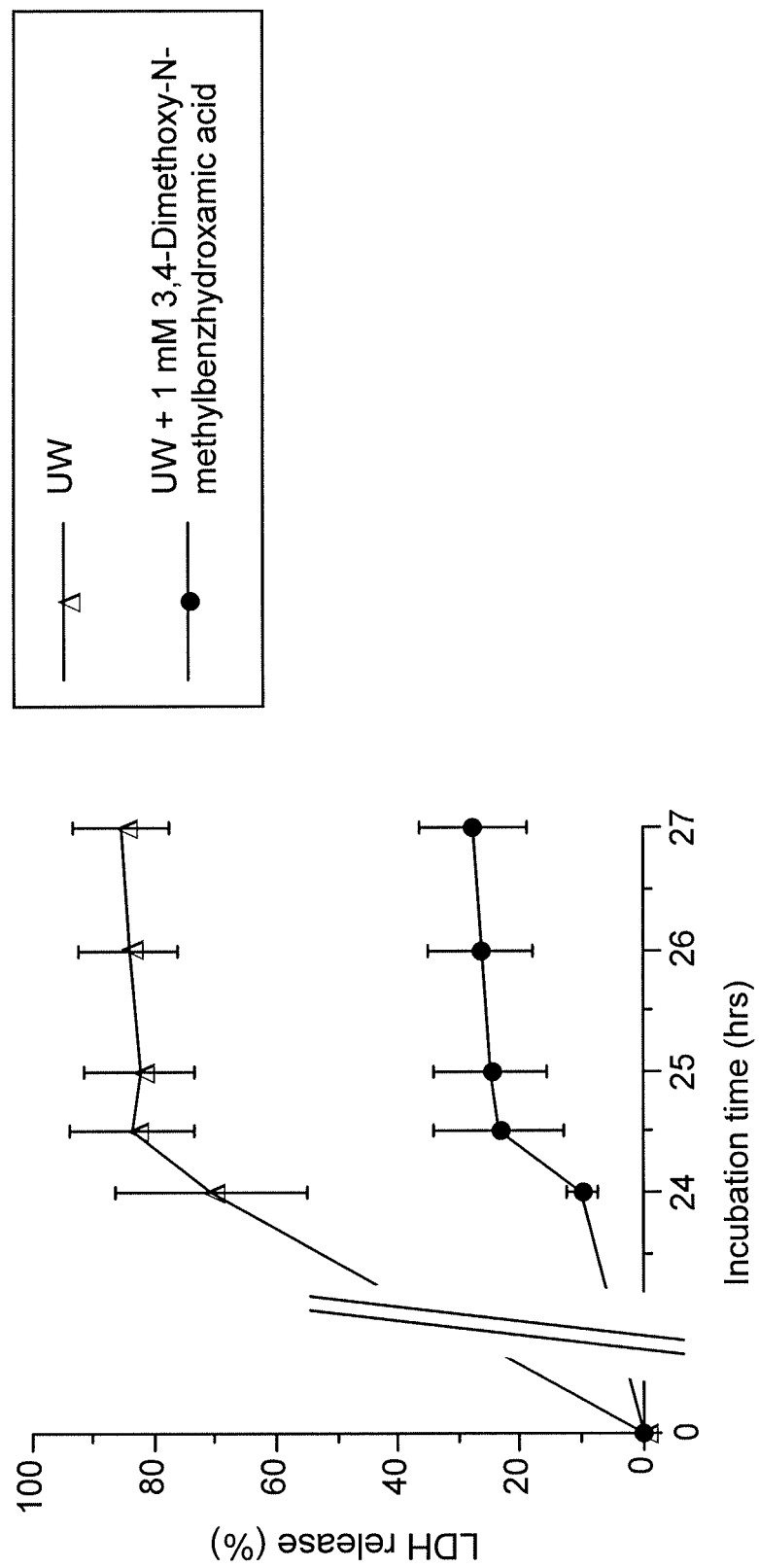
FIG. 2 is a graph showing the inhibition of hypothermic injury of hepatocytes by means of 3,4-dimethoxy-N-methyl-benzhydroxamic acid.

The effectiveness of two sample substances is demonstrated in FIGS. 1 and 2.

The hydroxamic acid, and/or derivatives can therefore be contained in the solutions according to the invention, purposefully at concentrations of up to about 10 mmol/l.

FIG. 1 shows the inhibition of hypothermic injury of liver endothelial cells by means of salicyl-N-methylhydroxamic acid. Cultivated rat liver endothelial cells were incubated for 72 hrs at 4° C. in University of Wisconsin solution (UW) under aerobic conditions in the presence of, and in the absence of 1 mM of salicyl-N-methylhydroxamic acid, and subsequently rewarmed for 3 hrs in a cell culture medium (37° C.). The release of cytosolic lactate dehydrogenase (LDH) served as the parameter of the cell damage.

FIG. 2 shows the inhibition of hypothermic injury of hepatocytes by means of 3,4-dimethoxy-N-methyl-benzhydroxamic acid. Cultivated rat hepatocytes were incubated for 24 hrs at 4° C. in a University of Wisconsin solution (UW) under aerobic conditions in the presence of, and in the absence of 1 mM of 3,4-dimethoxy-N-methyl-benzhydroxamic acid, and subsequently reheated for 3 hrs in a cell culture medium (37° C.). The secretion of cytosolic lactate dehydrogenesis (LDH) served as the parameter of the cell damage.

Deferoxamin is a strong iron-chelating agent, which as a hexadentate ligand binds iron in a non-redox-active form. It therefore serves as optimum protector for a longer period of hypothermic exposure. Deferoxamin, however, is a relatively large hydrophilic molecule with a correspondingly limited rate of membrane permeability. Deferoxamin therefore does not reach all intracellular compartments at a sufficient concentration and speed in order to provide complete protection. It can be contained in the solution at a concentration of preferably up to approximately 10 mmol/l.

Additional compounds that can be purposefully added to the organ protective solution according to the invention include one or more of the compounds and/or their salts from the groun acethydroxamic acid, acet-N-methylhydroxamic acid, N-benzylacethydroxamic acid, hexanehydroxamic acid, hexane-N-methylhydroxamic acid, benzohydroxamic acid, N-methylbenzohydroxamic acid, salicylhydroxamic acid, salicyl-N-methylhydroxamic acid, salicyl-N-benzylhydroxamic acid, 2-phenylacethydrox:amic acid, 2-phenylacet-N-methylhydroxamic acid, 3,4-dimethoxybenzohydroxamic acid, 3,4-dimethoxy-N-methyl-benzohydroxamic acid, 2,3-dihydroxybenzohydroxamic acid, 2,4-dihydroxybenzohydroxamic acid, 3,5-dimethoxy-N-methyl-benzohydroxamic acid, 2,4-dihydroxybeniohydroxamic acid, 2,3-dihydroxybenzohydroxamic acid, 3,4-dihydroxybeniohydroxamic acid, 3,4,5-trimethoxy-benzohydroxamic acid, 3,4,5-trimethoxy-N-methyl-benzohydroxamic acid, 4-hydroxy-3-methoxy-benzohydroxamnic acid, 2-hydroxy-3-methoxy-benzohydroxamic acid, 2-hydroxy-5-methoxy-benzohydroxamic acid, 2-hydroxy-3-methyl-isocarbostyril, 4-chloro-N-methyl-benzohydroxamic acid, 6-cyclohexyl-1-hydroxy-4-methyl-2(1H)-pvridone, and deferoxamin.

In another embodiment of the invention, a 6-hydroxy-2, 5,7,8-tetramethylchromane-2-carboxylic acid (trolox), or a derivative such as trolox-methylester is added to the solution. The relatively hydrophilic, but membrane-permeable radical scavenger trolox, or its derivatives, respectively, are added in order to scavenge intercept the intracellular radicals created during the hypothermic injury during the reoxygenation damage. Trolox or its derivative is purposefully present in the solution according to the invention at a concentration of up to approximately 10 mmol/l.

Figure 3:
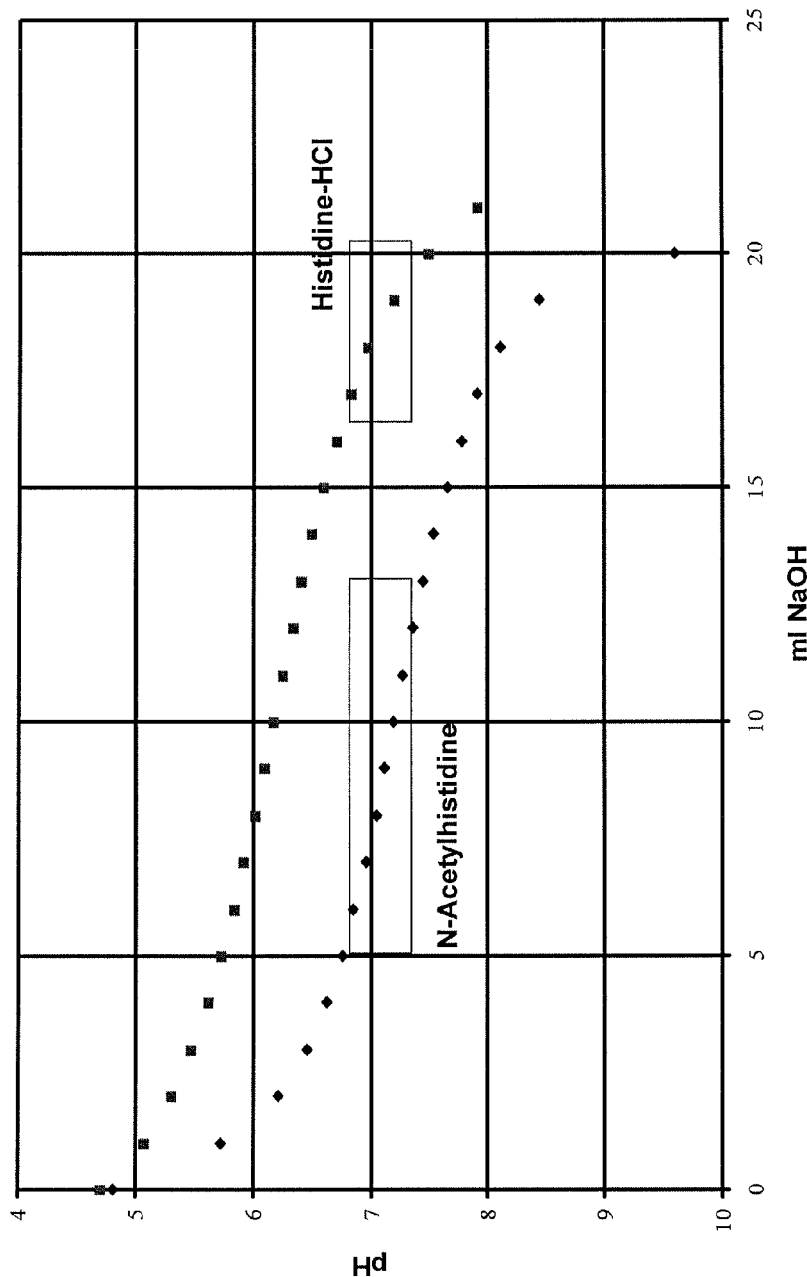
FIG. 3 is a graph showing the buffer capacity of N-acetyl-histidine compared to histidine/histidine HCl.

All organ preservation solutions have buffer substances that counteract the inevitable acidosis occurring during ischemia. Phosphates or bicarbonates are the most commonly used inorganic buffer systems for this purpose. The organic buffer system histidine/histidine-HCI used in Custodiol has proven as absolutely superior regarding the buffer capacity and pH stability. Particular advantages arise if derivatives of histidine, such as N-acetylhistidine, instead of histidine/histidine HCl are used as the buffer system in the aforementioned solution, but also in other known protective solutions. FIG. 3 shows the buffer capacity of N-acetylhistidine that is improved by the factor 2 as compared to histidine/histidine HCl. The substitution by N-acetylhistidine also avoids some undesired side effects of histidine (toxicity especially in the warmth, but also under hypothermic conditions in some cell types, such as in hepatocytes) without negatively influencing the good buffer capacity. (FIG. 4)

FIG. 3 shows the neutralization curve of histidine/histidine-HCl and N-acetylhistidine. The usable buffer capacity in the range of the physiological pH value; with N-acetylhistidine 60%, and with histidine 30% based on the ratio of spent base to substrate.

The said buffer system can be contained in the solution according to the invention at a concentration of preferably about 20 mmol/l to about 265 mmol/l.

Figure 4:
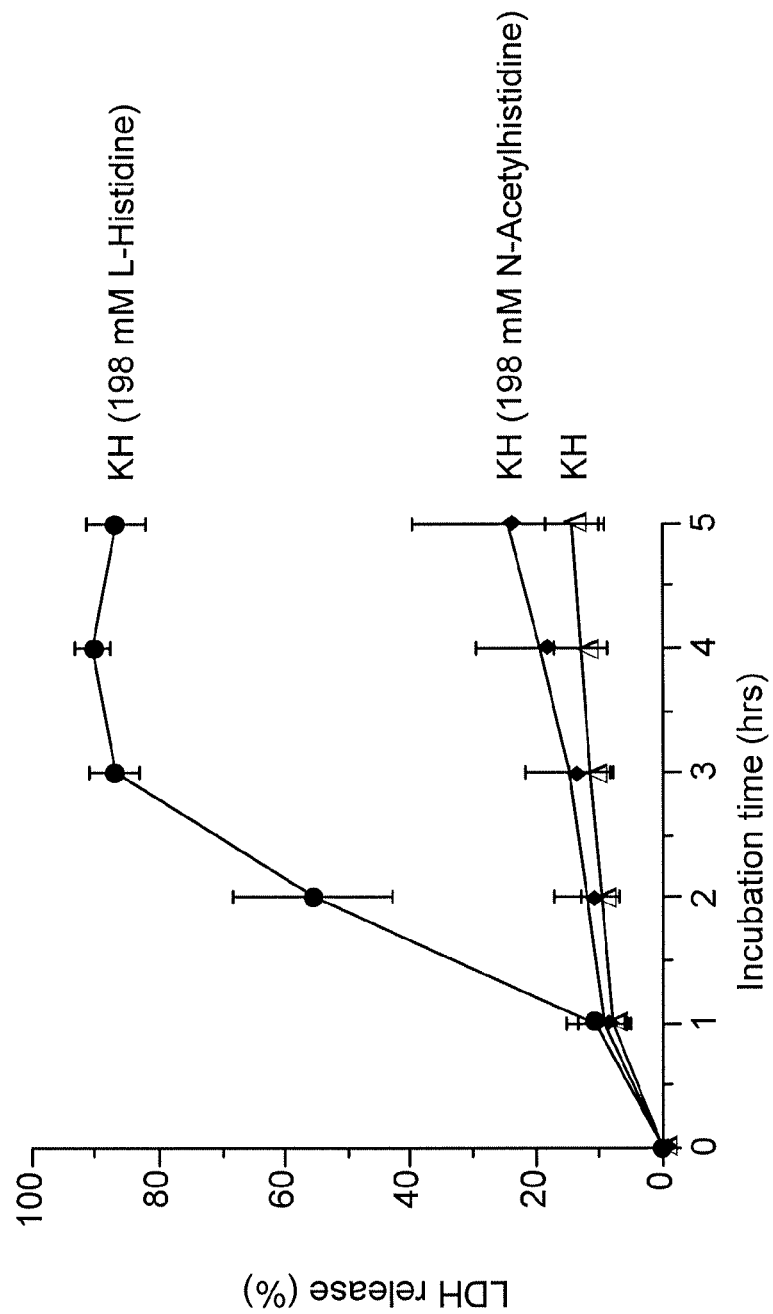
FIG. 4 is a graph showing the toxicity of histidine under warm conditions, and decrease of this toxicity by means of histidine derivatives.

FIG. 4 shows an example for the toxicity of histidine under warm conditions, and decrease of this toxicity by means of histidine derivatives. Cultivated rat hepatocytes were incubated for 5 hrs at 37° C. under aerobic conditions in the presence of, and in the absence of 198 mM of L-histidine, or 198 mM of N-acetylhistidine. The base solution was Krebs-Henseleit buffer (KH), a physiological saline solution often used in cell cultures; the NaCl concentration of the histidine (derivative) containing solution was decreased by 99 mM and the histidine (derivative) solution was adjusted by the addition of HCl or NAOH to pH 7.2.

These further developments allow an even better preservation of the cellular functions after preservation.

Purposefully, sodium ions are used as one of the cations. Relatively low sodium concentrations are advantageous for the electro-mechanical decoupling at the cell membrane (cardiac arrest) on one hand, and they reduce the hypoxic damage due to the avoidance/reduction of the hypoxia-induced sodium inflow, on the other hand. Furthermore, an osmotic reserve for other substances (such as buffer substances, see below) remains intact. Also, a rapid adjustment of the homeostasis is possible at a low sodium concentration of the solution, because the interstitial increase of sodium (140 mM) occurs rapidly. Therefore, a sodium concentration of about 10 mmol/to about 120 mmol/l is recommended in the solution according to the invention.

A relatively low, but above the physiological extracellular value lying potassium concentration supports the electromechanical isolation at the cell membrane (cardiac arrest), however, avoids the disadvantages of highly hyperkalaemic solutions (highly hyperkalaemic solutions induce rapid cardiac arrest, but are also responsible for arrhythmia and possibly increased reperfusion damage during the reoxygenation phase; the adjustment of the interstitial potassium concentration is time delayed during the reperfusion phase, which results in the increase of the quota of delayed initial functions of the organs with these type of solutions). Only slightly hyperkalaemic solutions possess the additional advantage that an elution of the solution from the organ to be transplanted is not necessary before the reperfusion (the solutions can thereby develop their protective properties up to the end of the ischaemia time), and have a high systemic tolerability. Therefore, a potassium concentration of about 5 mmol/l to about 25 mmol/l in the solution according to the invention is recommended.

A clearly increased magnesium concentration (beyond the standard serum value) is the goal, since magnesium supports the anaerobic metabolism as the cofactor of numerous glycolytic enzyme systems, and therefore contributes to the formation of ATP, even during the cold ischemia. Magnesium also contributes to the maintenance of the activity of the $Na^+$—$K^+$-ATPase of the plasma membrane, and thereby counteracts the changes in the ion homeostasis. As a physiological $Ca^{2+}$ antagonist, magnesium is also able to counteract the damaging effects of an intracellular calcium accumulation. A high concentration of magnesium is necessary during the reperfusion phase in order to stimulate the aerobic energy metabolism. The vascular dilative properties of magnesium additionally counteract the constrictive effects of reperfusion damage. Therefore, a magnesium concentration of about 3 mmol/l to about 27 mmol/l in the solution according to the invention is recommended.

The risk of a cytosolic calcium increase exists under ischemic conditions (and the associated intracellular acidosis and dysfunction of sodium homeostasis). This leads to an increase of undesired activities, such as the stimulation of proteases and phospholipases, and is associated in the heart with hypercontracture and a high ATP consumption. The physiological functions of calcium must therefore be inhibited as much as possible during ischaemia, which is why calcium concentration in the solution should be within the range of the cytoplasmic concentrations. Therefore, a free calcium concentration of about 0.0001 mmol/l to about 1.5 mmol/l is recommended in the solution according to the invention.

The basic amino acids lysine and arginine, or their derivatives as the dipeptides with glycine (lys-gly, gly-lys, or arg-gly, gly-arg) can be used to cover any lack of base equivalents, as the concentration and the ratio of the cations sodium, potassium, magnesium, and calcium are determined based on the above-described facts. The concentration of lysine and/or lysine derivatives, or arginine and/or arginine derivatives in the solution according to the invention may each be up to about 140 mmol/l.

The physiological extracellular anion chloride is used at a clearly lower concentration as compared to the physiological values in order to reduce any disturbance of the ion homeostasis during cold ischemia. This is true especially for a hypoxia-induced influx of cations, such as sodium. For reasons of electro-neutrality, this influx depends on the parallel influx of anions, preferably of chloride. Indications of different authors lead to the conclusion that high chloride concentrations benefit the extent of an intracellular edema. Therefore, a chloride concentration in the solution according to the invention of about 10 mmol/l to about 90 mmol/l is recommended. In addition to chloride, lactobionate may also be added as an impermeable anion at a concentration of up to about 140 mmol/l.

The concentrations of anions used in the organ-protective solutions are generally arrived at by the selection of cations and the inorganic buffer used. The use of impermeable anions, such as lactobionate, is meant to counteract the development of an intracellular edema. Aspartate represents an excellent alternative since several goals can be achieved with the use of aspartate:

a) Aspartate as replaces the unfavorable chloride.
b) Aspartate actively supports the substance exchange on membranes, and accelerates homeostasis regeneration.
c) Aspartate benefits the aerobic energy metabolism in the critical phase of reperfusion, or reoxygenation of the organ and accelerates its initial functions in combination with alpha-ketoglutarate.

Especially during the reoxygenation phase when the energy consumption increases substantially with an increased warming of the organ, it is necessary to force the energy supply, because a lack of ATP particularly during this warming phase would negatively influence the functionality of the organ substantially, and increase the extent of reperfusion damage. An aspartate concentration of up to about 140 mmol/l in the solution according to the invention is recommended. Purposefully, the solution according to the invention contains aspartate at a ratio in excess of chloride.

The amino acid glycine is used at a higher millimolar concentration, as glycine prevents the hypoxia-induced sodium influx by stabilizing the plasma membrane (prevention of a diffusion-oriented substance exchange) at these concentrations, and additionally inhibits the activation of macrophages. A glycine concentration of up to about 30 mmol/l is recommended in the solution according to the invention.

The energy consumption of the respective organ during the cold ischemia is also not insignificant, which is why energy supplying substrates or energy metabolism promoting substances are added to the solution for support. Different concepts are followed (also see aspartate above, and alpha-ketoglutarate below), one of which is the addition of glucose.

A physiological glucose concentration in the solution allows the cells, which are dependent on an exogenous glucose supply due to comparably lower glycogen reserves, such as endothelial cells, to gain energy via anaerobic glycolysis during ischemia. However, the glucose concentration is selected so that an excessive absorption of glucose by other cells, especially by hepatocytes (a problem with earlier preservation solutions using extremely high glucose concentrations) is avoided. Therefore, a glucose concentration of up to about 10 mmol/l is recommended in the solution according to the invention.

Together with aspartate, alpha-ketoglutarate serves to support the metabolism under/according to hypoxic conditions. Purposefully, a concentration of about 1 mmol/l to about 9 mmol/l is chosen.

The addition of osmotically active substances is required to the extent as is necessary to reach the required physiological osmotic pressure of approximately 300 mosm/L. Generally, polyol/saccharide (such as mannitol), or also high-molecular-weight substances (such as HES, dextran) are used for this purpose. The latter have not been well proven for some organs, because the disadvantages of the high viscosity created by HES and dextran negatively influence the quality of protection.

| Viscosity at 4° C. | |
|---|---|
| Custodiol | 1.8 cP |
| UW solution | 4.8 cP |

Depending on the organ, mannitol, xylitol, sorbitol, sucrose, or raffinose should be used as the osmolyte. Purposefully, the osmolyte concentration is up to 140 mmol/l in the solution according to the invention.

In order to avoid an interstitial edema, the addition of a colloid osmotically active substance is desirable in some organs/tissues. Dextran-40/dextran-70. This is especially true for lung and pancreas preservation.

For the cryopreservation of cells and tissue, the addition of additional cryoprotectants, such as dimethylsulfoxide (DMSO), is desirable.

Figure 5:
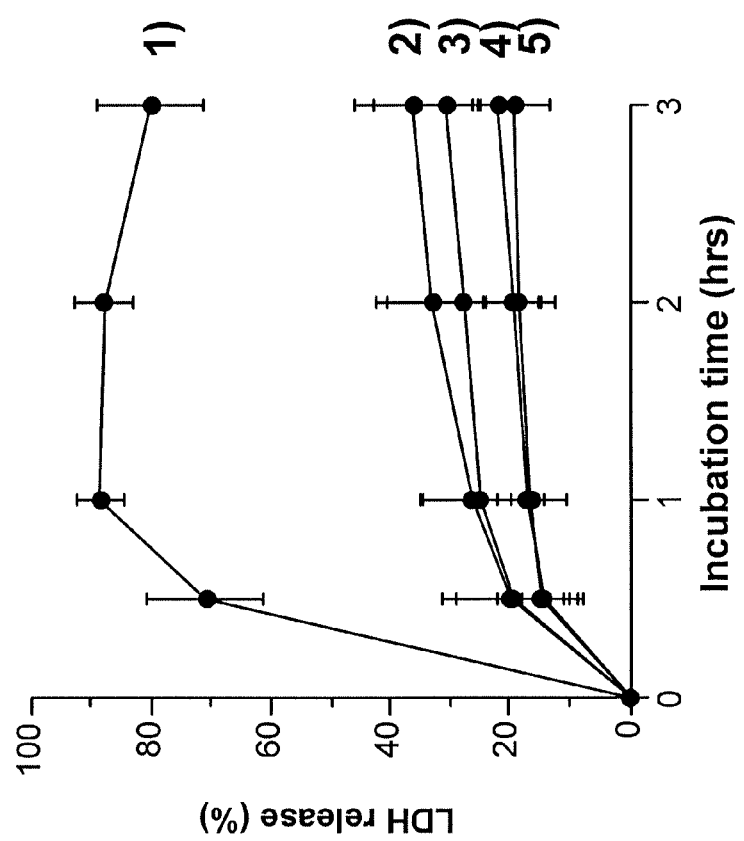
FIG. 5 is a graph showing the cell damage of hepatocytes by hydrogenperoxide and the protection thereof by various hydroxamic acids.

FIG. 5 shows the cell damage of hepatocytes by hydrogenperoxide and the protection thereof by various hydroxamic acids, wherein the graphs refer to graph no. 1: N4+20 mM/l $H_2O_2$ graph no. 2: N4+20 mM/l $H_2O_2$+1 mM/l 4-chloro-N-methyl-benzohydroxamic acid graph no. 3: N4+20 mM/l $H_2O_2$+1 mM/l 2-hydroxy-3-methyl-isocarbosteryl graph no. 4: N4+20 mM/l $H_2O_2$+1 mM/l 3,4,5-trimethoxy-N-methyl-benzohydroxamic acid graph no. 5: N4+20 mM/l $H_2O_2$+1 mM/l 3,4-dimethoxy-N-methyl-hydroxamic acid, N4 meaning the solution according to example II given hereinafter, but without Trolox and without hydroxamic acid derivative.

Figure 6:
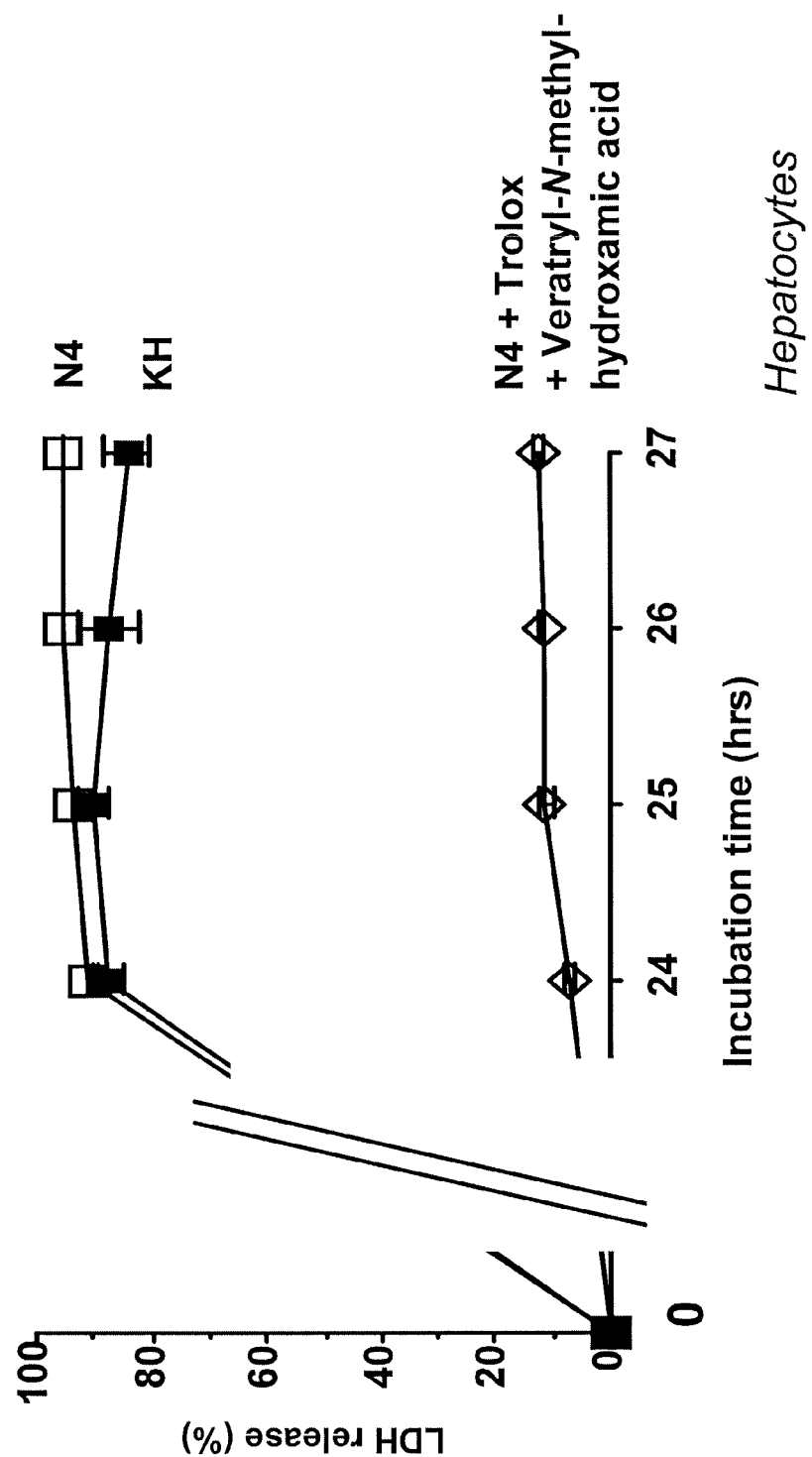
FIG. 6 is a graph showing the inhibition of hypothermic injury of hepatocytes by the solution of the invention.

FIG. 6 shows the inhibition of hypothermic injury of hepatocytes by the new solution. Cultured hepatocytes were incubated for 24 hrs at 4° C. in a solution (with N-acetyl-histidine as buffer and with trolox, 1 mM, and a hydroxamic acid derivative, Veratryl-N-methylhydroxamic acid, 0.5 mM) and for comparison in Krebs-Henseleit buffer (KH). Cold incubation was performed under aerobic conditions; after 24 hrs cells were rewarmed—for the simulation of reperfusion—in cell culture medium at 37° C. The release of cytosolic lactate dehydrogenase (LDH) served as marker of cell injury.

EXAMPLES

The following illustrates some examples of solutions that meet the requirements of the protective scope claimed herein:

Example I

| | mmol/l |
|---|---|
| $Na^+$ | 25 |
| $K^+$ | 15 |
| $Mg^{++}$ | 10 |
| $Ca^{++}$ | 0.1 |
| $Cl^-$ | 25 |
| Aspartate$^-$ | 33 |
| Ac-N-His | 60 |
| Ac-N-His$^-$ | 60 |
| Lysine-H$^+$ | 60 |
| Glycine | 10 |
| Tryptophan | 2 |
| Veratryl-N-methylhydroxamic acid | 2 |
| Trolox-OCH$_3$ | 2 |
| Ketoglutarate | 2 |
| N-methylsalicylic hydroxamic acid | 2 |
| pH | 7.2 |
| Osmolarity | 310 |

Example II

| | mmol/l |
|---|---|
| Na(+) | 15 |
| K(+) | 10 |
| Mg(++) | 8 |
| Ca(++) | 0.015 |
| Cl(−) | 0.03 |
| Aspartate(−) | 38 |
| Ac-N-His | 60 |
| Ac-N-His(−) | 60 |
| Lysin-H(+) | 60 |
| Glycine | 10 |
| Tryptophan | 2 |
| 2,3-Dimethoxy-N-methylbenzhydroxamacid | 2 |
| Trolox | 2 |
| Ketoglutarat(−) | 3 |
| N-Methylsalicylhydroxamacid | 2 |
| Mannitol | 30 |
| pH | 7.2 |
| Osmolarity | 310 |

Example III

| | mmol/l |
|---|---|
| Na(+) | 15 |
| K(+) | 10 |
| Mg(++) | 16 |
| Ca(++) | 0.04 |
| Cl(−) | 0.03 |
| Aspartate(−) | 54 |
| Ac-N-His | 60 |

-continued

|  | mmol/l |
|---|---|
| Ac-N-His (−) | 60 |
| Lysin-H(+) | 60 |
| Glycine | 6 |
| Tryptophan | 2 |
| 2,3-Dimethoxy-benzhydroxamacid | 1 |
| Trolox | 2 |
| Ketoglutarate(−) | 3 |
| 2-Hydroxy-3-methyl-isocarbostryril | 1 |
| Mannitol | 20 |
| PH | 7.2 |
| Osmolarity | 310 |

Example IV

|  | mmol/l |
|---|---|
| Na(+) | 15 |
| K(+) | 10 |
| Mg(++) | 8 |
| Ca(++) | 0.015 |
| Cl(−) | 0.03 |
| Aspartate(−) | 31 |
| Ac-N-His | 70 |
| Ac-N-His (−) | 70 |
| Lysine-H(+) | 70 |
| Glycine | 8 |
| Tryptophan | 2 |
| 2-Hydroxy-3-methyl-isocarbostryril | 2 |
| Ketoglutarate(−) | 2 |
| N-Methylsalicylhydroxamacid | 2 |
| Mannitol | 20 |
| PH | 7.2 |
| Osmolarity | 310 |

Example V

|  | mmol/l |
|---|---|
| Na(+) | 16 |
| K(+) | 10 |
| Mg(++) | 8 |
| Ca(++) | 0.05 |
| Cl(−) | 0.1 |
| Aspartate | 16 |
| N-Ac-His | 80 |
| Histidine | 88 |
| L-Arginine | 12 |
| Glycine | 20 |
| L-Alanine | 10 |
| Tryptophan | 2 |
| Alpha-Ketoglutarate | 3 |
| Mannitol | 40 |
| 3,4-Dimethoxy-N-methyl-hydroxamacid | 2 |
| PH | 7.3 |
| Osmolarity | 307 |

The solution according to the invention is produced according to the functional components of an organ-preservative solution, namely the buffer system, electrolytes, protectively active substances, and osmolyte. For this purpose the buffer substances are initially diluted in approximately 90% of the required amount of water. The neutral salts of the cations necessary as the electrolytes, i.e., sodium, potassium, magnesium, and calcium, for instance, is then added at the stated physiologically reasonable concentrations, and stirred until it is dissolved. As the additional components, the protectively active substances are then added to the solution. The pH value is then checked, and adjusted to a pH value of about 6.8 to about 7.4, if necessary. Finally, the stated amount of osmolyte is added, and the solution is diluted to its desired volume. After filling it into suitable containers, the solution is sterilized.

The production of cyclic hydroxamic acid, for instance the compounds derived from 2-hydroxypyridine-N-oxide, is described, for example, in Organic Synthesis Collective, Volume V, page 623 and following pages. A production method of hydroxamic acids made from carboxylic acid derivatives is found in Houben-Weyl, Methods for Organic Chemistry, page 686 and following pages, whereby short alcohols, DMF, THF are used as the solvents. The reaction using the respective carbonic acid ester can occur in an alkaline catalyzed manner (NaOMe, $K_2CO_3$, CaO). Finally, with the production of cyclic hydroxamic acid reference is made to A. Kleemann, J. Engel, Pharmaceutical Active Agents, second edition 1982, page 206 and following pages.

The invention claimed is:

1. A protective solution for avoiding ischemic damage to organs, or to isolated cell systems, or to tissue components after perfusion, surgery, transplantation, or cryoconservation and subsequent reperfusion, which solution comprises the following components:
   (i) sodium at a concentration of about 10 mmol/l to about 120 mmol/l;
   (ii) magnesium at a concentration of about 3 mmol/l to about 27 mmol/l;
   (iii) calcium at a concentration of about 0.0001 mmol/l to about 1.5 mmol/l;
   (iv) chloride;
   (v) n-acetyl histidine;
   (vi) sucrose;
   (vii) a-ketoglutarate at a concentration of about 1 mmol/l to about 9 mmol/l;
   (viii) aspartate in an amount in excess of chloride;
   (ix) glycine;
   (x) arginine;
   (xi) deferoxamine; and
   (xii) 3,4-dimethoxy-N-methyl-benzohydroxamic acid;
   wherein said solution has an osmolarity of about 290 Osm/l to about 350 mOsm/l, as well as a pH value of about 6.8 to about 7.4;
   wherein the maximum concentration of aspartate is about 140 mmol/l;
   wherein the maximum concentration of arginine is about 140 mmol/l;
   wherein the maximum concentration of deferoxamine is about 10 mmol/l; and
   wherein the maximum concentration of 3,4-dimethoxy-N-methyl-benzohydroxamic acid is about 10 mmol/l.

2. The solution according to 1, wherein the solution contains potassium ions at a concentration of about 5 mmol/l to about 25 mmol/l.

3. A protective solution for avoiding ischemic damage to organs, or to isolated cell systems, or to tissue components after perfusion, surgery, transplantation, or cryoconservation and subsequent reperfusion, which solution comprises the following components:
   (i) sodium at a concentration of about 10 mmol/l to about 120 mmol/l;
   (ii) magnesium at a concentration of about 3 mmol/l to about 27 mmol/l;
   (iii) calcium at a concentration of about 0.0001 mmol/l to about 1.5 mmol/l;
   (iv) chloride;

(v) n-acetyl histidine;
  (vi) sucrose;
  (vii) a-ketoglutarate at a concentration of about 1 mmol/l to about 9 mmol/l;
  (viii) aspartate;
  (ix) glycine;
  (x) arginine;
  (xi) deferoxamine; and
  (xii) 3,4-dimethoxy-N-methyl-benzohydroxamic acid;
wherein said solution has an osmolarity of about 290 mOsm/l to about 350 mOsm/l, as well as a pH value of about 6.8 to about 7.4.

4. A solution comprising:
  (i) sodium at a concentration of about 10 mmol/l to about 120 mmol/l;
  (ii) magnesium at a concentration of about 3 mmol/l to about 27 mmol/l;
  (iii) calcium at a concentration of about 0.0001 mmol/l to about 1.5 mmol/l;
  (iv) chloride;
  (v) n-acetyl histidine;
  (vi) sucrose;
  (vii) a-ketoglutarate at a concentration of about 1 mmol/l to about 9 mmol/l;
  (viii) aspartate in an amount in excess of chloride;
  (ix) glycine;
  (x) arginine;
  (xi) deferoxamine; and
  (xii) 3,4-dimethoxy-N-methyl-benzohydroxamic acid;
wherein said solution has an osmolarity of about 290 mOsm/l to about 350 mOsm/l, as well as a pH value of about 6.8 to about 7.4;
wherein the maximum concentration of aspartate is about 140 mmol/l;
wherein the maximum concentration of arginine is about 140 mmol/l;
wherein the maximum concentration of deferoxamine is about 10 mmol/l; and
wherein the maximum concentration of 3,4-dimethoxy-N-methyl-benzohydroxamic acid is about 10 mmol/l.

5. A solution comprising:
  (i) sodium at a concentration of about 10 mmol/l to about 120 mmol/l;
  (ii) magnesium at a concentration of about 3 mmol/l to about 27 mmol/l;
  (iii) calcium at a concentration of about 0.0001 mmol/l to about 1.5 mmol/l;
  (iv) chloride;
  (v) n-acetyl histidine;
  (vi) sucrose;
  (vii) a-ketoglutarate at a concentration of about 1 mmol/l to about 9 mmol/l;
  (viii) aspartate;
  (ix) glycine;
  (x) arginine;
  (xi) deferoxamine; and
  (xii) 3,4-dimethoxy-N-methyl-benzohydroxamic acid;
wherein said solution has an osmolarity of about 290 mOsm/l to about 350 mOsm/l, as well as a pH value of about 6.8 to about 7.4.

* * * * *